US00PP21116P2

(12) United States Plant Patent
Jensen

(10) Patent No.: US PP21,116 P2
(45) Date of Patent: Jun. 29, 2010

(54) *ASTER* PLANT NAMED 'DASDEM'

(50) Latin Name: *Aster novi-belgi*
Varietal Denomination: DASDEM

(75) Inventor: Bent Juhl Jensen, Malling (DK)

(73) Assignee: Gartneriet Raahoj, Malling (DK)

( * ) Notice: Subject to any disclaimer, the term of this patent is extended or adjusted under 35 U.S.C. 154(b) by 0 days.

(21) Appl. No.: 12/380,356

(22) Filed: Feb. 26, 2009

(51) Int. Cl.
*A01H 5/00* (2006.01)

(52) U.S. Cl. ..... Plt./355

(58) Field of Classification Search ..... Plt./355
See application file for complete search history.

(56) References Cited

OTHER PUBLICATIONS

UPOV-ROM GTITM, Plant Variety Database, 2009/05, GTI Jouve Retrieval Software, citation for 'DASDEM'.*
Print-out of application number and filing date from Community Plant Variety Office (CPVO) website for corresponding, CPVO application No. 2007/2429 filed Nov. 5, 2007, together with copy of Assignment filed Jan. 23, 2009 (8 pages). (http://www.cpvoextranet.cpvo.europa.eu).

* cited by examiner

*Primary Examiner*—Susan B McCormick Ewoldt
(74) *Attorney, Agent, or Firm*—Foley & Lardner LLP

(57) ABSTRACT

A new distinct cultivar of *Aster* plant named 'DASDEM', characterized by its upright plant form with somewhat outward spreading plant habit; bright yellow-green foliage; decorative, composite-type inflorescence with about 250 violet-blue colored ray florets; and only about 10 to 20 green-colored disc florets per inflorescence (almost 100% filled capitulae).

3 Drawing Sheets

Latin name of the genus and species of the claim plant: *Aster novi-belgi* (now *Symphyotrichum novi-belgii*).

Variety denomination: 'DASDEM'.

BACKGROUND OF THE INVENTION

The present invention relates to a new and distinct cultivar of *Aster* plant, botanically known as *Aster novi-belgii* (now *Symphyotrichum novi-belgii*) of the Asteraceae family, commonly known as the Michaelmas Daisy and New York Aster, and hereinafter referred to by the cultivar name 'DASDEM'.

The new *Aster* cultivar is a product of a planned breeding program conducted by the inventor, Bent Juhl JENSEN, in Malling, Denmark. The objective of the breeding program is to develop a new *Aster* variety with uniform plant growth habit, unique floret colors, and good postproduction longevity.

The new *Aster* cultivar originated from a cross made in a controlled breeding program by the inventor on Apr. 1, 2005 in Malling, Denmark. The female or seed parent is *Aster novi-belgii* 'MILKA' (patented, U.S. Plant Pat. No. 10,602). The male or pollen parent is *Aster novi-belgii* 'MARGRETHE VIKING' (patented, U.S. Plant Pat. No. 10,358 and CPVO Grant No. 8378). The new *Aster* 'DASDEM' was discovered and selected by the inventor as a single flowering plant within the progeny of the stated cross in September of 2006 in a controlled environment in Malling, Denmark. The selection of the new *Aster* 'DASDEM' was based on its uniform plant growth habit and desirable inflorescence form and ray floret color.

Asexual reproduction of the new *Aster* cultivar by vegetative tip cuttings was first performed in June of 2006 in Malling, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DASDEM', which in combination distinguish this *Aster* as a new and distinct cultivar:

1. Upright plant form with somewhat outward spreading plant habit;
2. Bright yellow-green foliage;
3. Decorative, composite-type inflorescence with about 250 violet-colored ray florets; and
4. Only about 10 to 20 green-colored disc florets per inflorescence (almost 100% filled capitulae).

Plants of the new *Aster* 'DASDEM' differ from plants of the parents, *Aster* 'MILKA' (patented, U.S. Plant Pat. No. 10,602) and *Aster* 'MARGRETHE VIKING' (patented, U.S. Plant Pat. No. 10,358 and CPVO Grant No. 8378) in the characteristics described in Table 1.

TABLE 1

| Characteristic | New Cultivar 'DASDEM' | Female Parent 'MILKA' (patented) | Male Parent 'MARGRETHE VIKING' (patented) |
|---|---|---|---|
| Leaf Shape: | Gladiate to linear | Elliptic | Elliptic |
| Mature Leaf Color (upper surface): | Yellow-green, RHS 147A | Green, RHS 137A to RHS 137B | Green, RHS 137A |
| Capitulum Size: | Diameter: 32-35 mm | Diameter: 24-27 mm | Diameter: 30-35 mm |

TABLE 1-continued

| Characteristic | New Cultivar 'DASDEM' | Female Parent 'MILKA' (patented) | Male Parent 'MARGRETHE VIKING' (patented) |
|---|---|---|---|
| Ray Florets | About 250 florets per inflorescence, which are oval in shape, with rounded, slightly retuse apex | About 128-164 ray florets per flower, which are narrowly elliptic in shape, with acute apex | About 100-150 ray florets per flower, which are narrowly obovate in shape, with obtuse apex |
| Mature Ray Floret Color (upper surface): | Violet, RHS 84C | Violet, RHS 85A | White, RHS 155D |
| Disc Florets: | About 10-20 disc florets per inflorescence | No disc florets produced. | About 35-45 disc florets per inflorescence |
| Mature Disc Floret Color: | Green | N/A | Purple |

Of the many commercial cultivars known to the present inventor, the most similar in comparison to the new *Aster* 'DASDEM' are 1) *Aster novi-belgii* 'VICTORIA FANNY' (patented, U.S. Plant Pat. No. 13,360 and CPVO Grant No. 11804) and 2) *Aster novi-belgii* 'VICTORIA ILONA' (patented, CPVO Grant No. 14581). Plants of the new *Aster* 'DASDEM' differ from plants of *Aster novi-belgii* 'VICTORIA FANNY' and *Aster novi-belgii* 'VICTORIA ILONA' in the characteristics described in Table 2.

TABLE 2

| Characteristic | New Cultivar 'DASDEM' | Comparison Cultivar 'VICTORIA FANNY' (patented) | Comparison Cultivar 'VICTORIA ILONA' (patented) |
|---|---|---|---|
| Leaf Shape: | Gladiate to linear | Lanceolate | Gladiate to lanceolate |
| Mature Leaf Color (upper surface): | Yellow-green, RHS 147A | Yellow-green, RHS 147A | Green, RHS 139B |
| Capitulum Size: | Diameter: 32-35 mm | Diameter: 32.5 mm | Diameter: 32.5 mm |
| Ray Florets | About 250 ray florets per inflorescence, which are oval in shape, with rounded, slightly retuse apex | About 190 ray florets per flower, which are narrowly obovate in shape, with rounded apex | About 250 to 300 ray florets per flower, which are lanceolate in shape, with rounded apex |
| Mature Ray Floret Color (upper surface): | Violet, RHS 84C | Violet, RHS 88C | Purple, RHS 76B |
| Disc Florets: | About 10-20 disc florets per inflorescence | About 25-35 disc florets per inflorescence | About 50-60 disc florets per inflorescence |
| Mature Disc Floret Color: | Green, RHS 137D | Yellow-green, RHS 151B | Green, RHS 137D |

BRIEF DESCRIPTION OF THE PHOTOGRAPHS

The accompanying photographs illustrate the overall appearance of the new *Aster* 'DASDEM' showing the colors as true as is reasonably possible with colored reproductions of this type. Colors in the photographs may differ slightly from the color value cited in the detailed botanical description which accurately describes the color of 'DASDEM'.

DETAILED BOTANICAL DESCRIPTION

Figure 1:
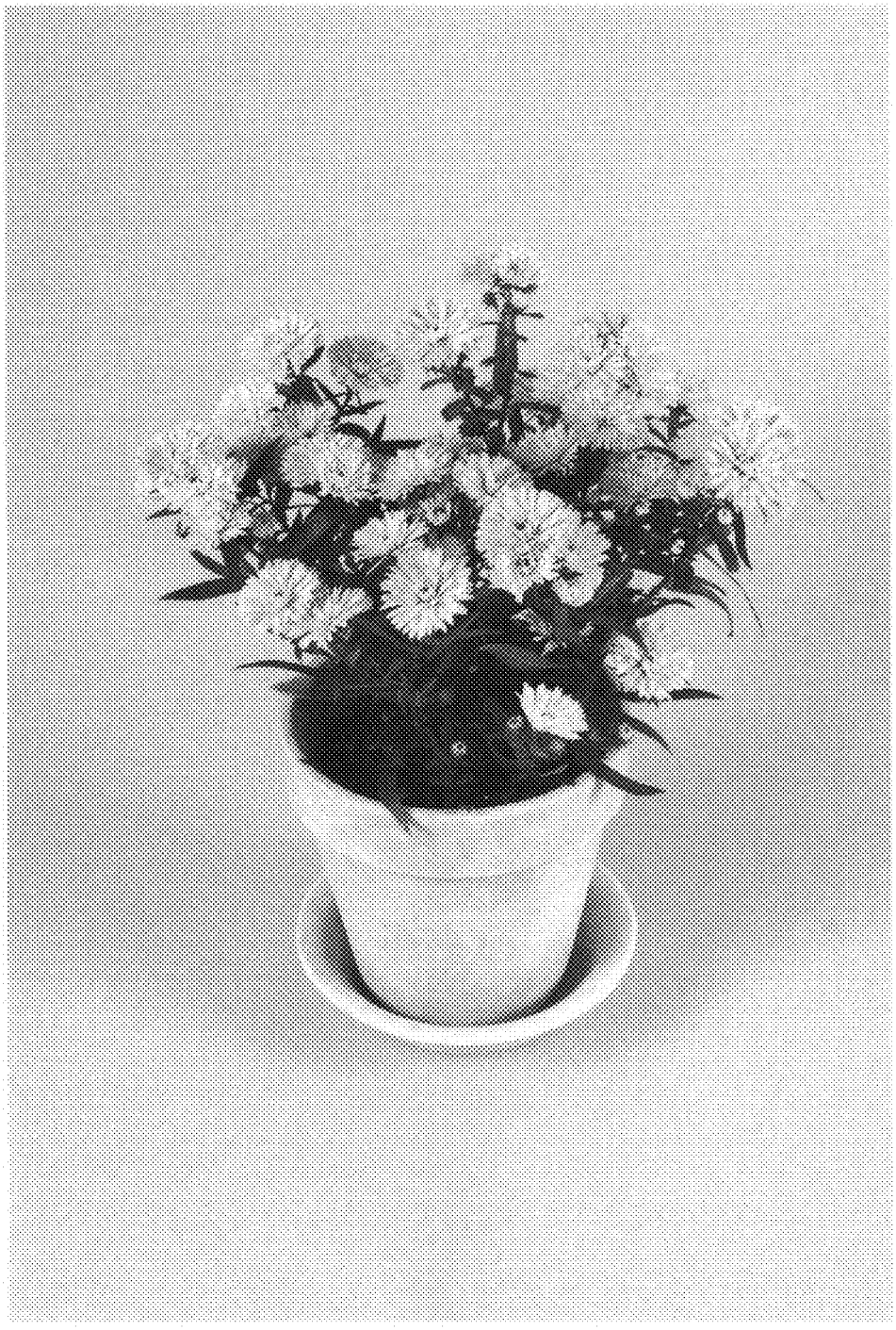
FIG. 1 shows a side view perspective a typical flowering plant of 'DASDEM' in a 9.5 cm pot, at 10 weeks of age after planting.
Figure 2:
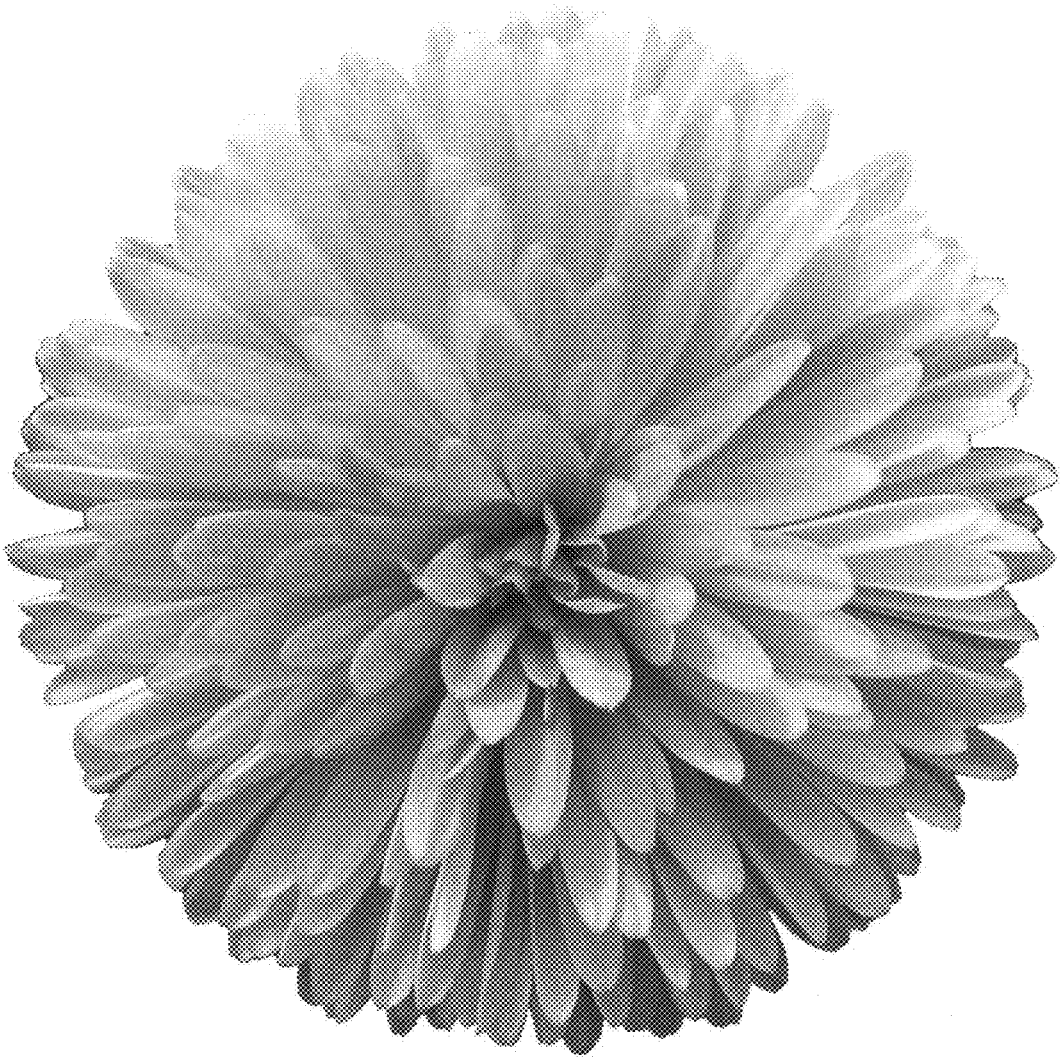
FIG. 2 shows a close-up view perspective of a typical mature inflorescence of 'DASDEM', at 10 weeks of age after planting.
Figure 3:
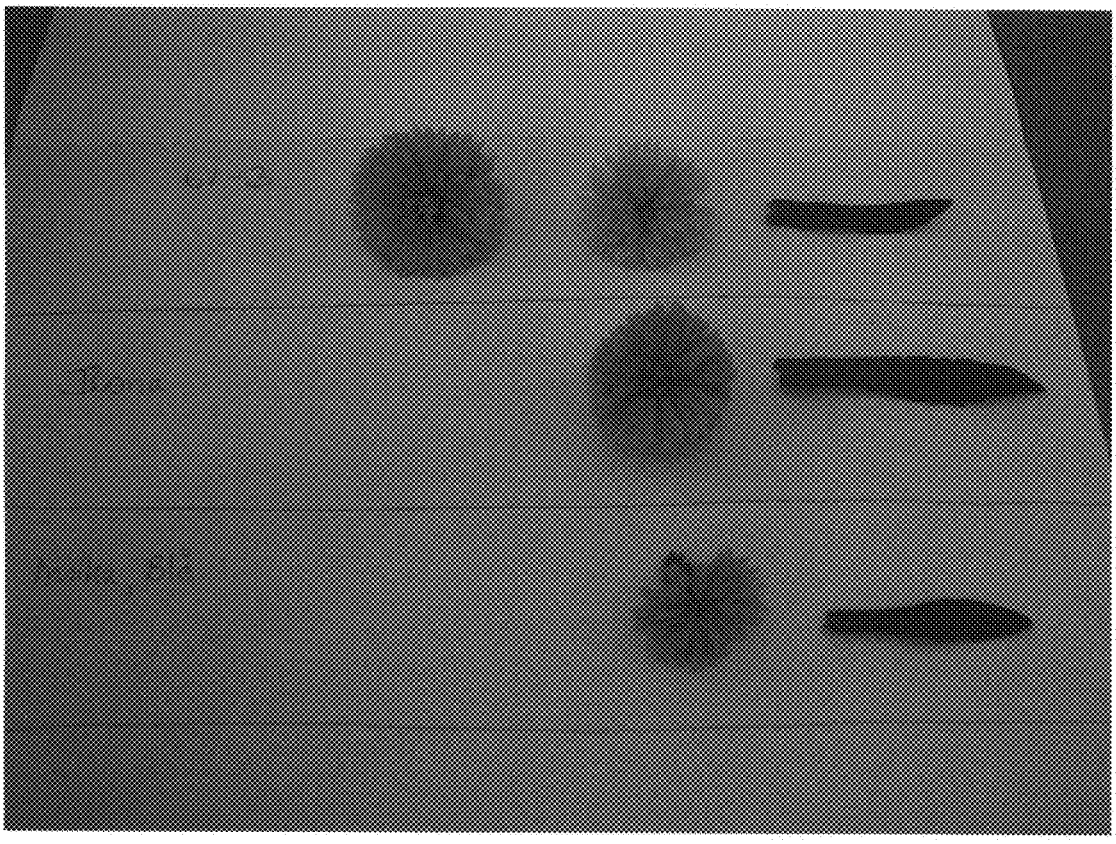
FIG. 3 shows a close-up comparison view of a typical mature inflorescence and leaf of: 1) the new *Aster* 'DASDEM' (referenced by breeder designation 61-3), compared to 2) the comparison cultivar *Aster* 'VICTORIA ILONA' (referenced by ILONA) and 3) the maternal cultivar *Aster* 'MILKA'.

The new *Aster* 'DASDEM' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Aster* 'DASDEM' as grown in a glass-covered greenhouse in Malling, Denmark, under conditions which closely approximate those generally used in commercial practice. 'DASDEM' plants were grown in 9.5 cm pots in a heated and lighted glass-covered greenhouse with the day temperatures ranging from 18° C. to 20° C. and the night temperature averaging 18° C. 'DASDEM' plants are grown under long day (20 hour) photoperiodic treatments for five weeks, followed by short day (12 hour) photoperiodic treatments for five weeks. During the long day (20 hour) photoperiodic treatments, if ambient light level falls below +50 $Wm^2$, a supplementary light at +200 $Wm^2$ is applied. 'DASDEM' plants 'DASDEM' plants were pinched once, and treated twice with the growth retardant Daminozide.

Color references are made to The Royal Horticultural Society Colour Chart (RHS), 4th Edition, except where general colors of ordinary significance are used. Color values were taken under daylight conditions in Malling, Denmark. The age of the 'DASDEM' plants shown in the photographs and described herein is about 10 weeks.

Classification:

*Botanical.*—*Aster novi-belgii* (now *Symphyotrichum novi-belgii*).

Parentage:

*Female or seed parent.*—*Aster novi-belgii* 'MILKA' (patented, U.S. Plant Pat. No. 10,602).

*Male or pollen parent.*—*Aster novi-belgii* 'MARGRETHE VIKING' (patented, U.S. Plant Pat. No. 10,358 and CPVO Grant No. 8378).

Propagation:

*Type.*—Vegetative tip cuttings.

*Time and temperature to initiate roots.*—Summer: About 12 days at 21° C. Winter: About 13 days at 21° C.

*Rooting habit.*—Fine, fibrous and freely branching.

*Root color.*—Gray-white, close to RHS 156D.

Plant description:

*General appearance and form.*—Herbaceous, decorative-type potted or bedding plant with upright plant habit. *Aster* inflorescences in composite heads.

*Growth and branching habit.*—Stems upright and somewhat outward spreading habit; inverted conical plant habit. Appropriate for 9 cm to 15 cm containers.

*Growth rate/vigor.*—Vigourous.

*Plant height* (*soil level to top of plant plane*).—About 17 cm.

*Plant width* (*spread*).—About 22 cm to 25 cm.

*Crop time to produce a mature flowering plant.*—After rooting, about 10 weeks are required to produce finished flowering plants in 9.5 cm pots.

Branches:

*Number of branches per plant.*—About 12, with 3 cuttings per pot.

*Quantity of buds and inflorescence per lateral stem.*—About 2 to 6, buds continue to develop when dead flowers are removed.

*Branching habit.*—Freely after pinching.

*Length.*—About 12 cm (including flowers).

*Diameter.*—About 2 mm.

*Internode length.*—About 9 mm. Range about 7 mm to 13 mm.

*Strength.*—Strong.

*Aspect.*—Upright.

*Texture.*—Slightly ridged and strigilose.

*Color.*—Green, RHS 137B.

Foliage description:

*Quantity per branch.*—About 10 to 14.

*Arrangement.*—Single, alternate, sessile.

*Length.*—Up to 6 cm.

*Width.*—Up to 8 mm.

*Overall shape of leaf.*—Gladiate to linear.

*Shape at apex.*—Acute.

*Shape at base.*—Decurrent, auriculate ½ clasping.

*Margin.*—Entire.

*Texture.*—Glabrous, smooth, leathery.

*Pubescence.*—Few short hairs on edges and abaxial surface.

*Color of developing foliage.*—Upper surface: Yellow-green, RHS 147A. Under surface: Gray-green, RHS 189A.

*Color of mature foliage.*—Upper surface: Yellow-green, RHS 147A. Under surface: Gray-green, RHS 191A.

*Venation pattern.*—None, but prominent central abaxial vein.

*Venation color.*—Upper surface: Yellow-green, RHS 147A. Under surface: Yellow-green, RHS 146C.

Inflorescence description:

*Appearance.*—Terminal and axillary composite inflorescences held above and beyond the foliage, with about 250 lanceolate-shaped ray florets and only about 10 to 20 disc florets; ray and disc florets arranged acropetally on a capitulum. Inflorescences face upright and form is capitulate in tight cymes.

*Natural flowering season.*—Under natural season conditions, plants flower in late summer through autumn in Denmark. Season can be extended by vernalization and long day treatments.

*Time to flower.*—About 5 to 6 weeks (longevity of individual inflorescences is dependent on temperature and light conditions).

*Postproduction longevity.*—Inflorescences maintain good color and substance for about 37 days on the plant when in an indoor environment, and may keep longer if temperatures are maintained below 20° C. Inflorescences persistent.

*Quantity of inflorescences.*—About 50 to 80 buds and open inflorescences per plant.

*Fragrance.*—Faint.

*Bud.*—Rate of opening: About 10 per week, for 3 weeks after induction. Length: Up to 7 mm. Diameter: Up to 7 mm. Shape: Globular. Texture: Glabrous. Color: Green, RHS 137B.

*Peduncle.*—Length: About 10 mm to 15 mm. Diameter: 1 mm. Appearance and angle: About 70° from vertical. Strength: Strong. Texture: Glabrous. Color: Green, RHS 134C.

*Inflorescence.*—Inflorescence depth (height): About 6 to 8 cm. Inflorescence diameter About 4 to 6 cm. Capitulum height: About 3.2 to 3.5 cm. Capitulum diameter: About 1.5 cm.

*Quantity of flowers* (*capitulae*) *per inflorescence.*—About 3 to 8 capitulae

*Inflorescence.*—Inflorescence height: About 5 to 6 cm. Inflorescence diameter About 6 to 7 cm. Capitulum height: About 15 mm. Capitulum diameter: About 35 mm.

*Ray florets.*—Arrangement and Quanity: Imbricate, about 250 ray florets per capitulum in 9 to 12 whorls of ray florets (depending on light and temperature conditions). Orientation: Initially upright, later mostly horizontal. Aspect: Straight to slightly involute. Appearance: Lanceolate. Length: About 7 mm to 9 mm. Width: About 2 mm. Overall shape: Oval. Shape at apex: Rounded, slighlty retuse. Shape at base: Fused. Margin: Entire. Texture: Upper and under surfaces: Smooth, glabrous. Pubescence: Subtended by numerous short, about 2 mm white hairs. Color (when opening): Upper surface: violet-blue, RHS 91D. Under surface: violet-blue, RHS 92D. Color (when fully opened): Upper surface: violet, RHS 84C. Under surface: violet-blue, RHS 92D. Fading: Yes, to violet-blue, RHS 92D.

*Disc florets.*—Arrangement: About 10 to 20 disc florets, massed at center of capitulum. Length: About 1 to 2 mm. Width: About 1 mm. Disc area diameter: About 2 mm. Overall shape: Tubular, elongated. Shape at apex: Acute. Shape at base: Fused to tube. Margin: Entire. Texture: Upper and under surfaces: Scale-like, parchment thin. Pubescence: Subtended by numerous short, about 2 mm, white hairs. Color (when opening): Upper and under surfaces: Green, RHS 137D. Color (when fully opened): Upper and under surfaces: Green, RHS 137D.

*Phyllaries.*—Quantity per inflorescence: Involucre, about 40 to 50. Length: About 3 to 5 mm. Width: About 1 to 2 mm. Overall shape: Tubular, elongated. Apex shape: Acute. Base shape: Fused lanceloate. Margin: Entire. Texture: Hairy, setulose edges, verrucose abaxial surface. Color (immature): Upper surface: Green, RHS 137B. Under surface: Green, RHS 137D. Color (immature): Upper surface: Green, RHS 137A. Under surface: Green, RHS 137B.

Reproductive organs:

*Androecium* (*on disc florets only*).—Stamen number: 1 per floret; fused around style. Stamen length: About 1 mm. Anther shape: Narrowly cylindrical, somewhat fused. Anther length: About 0.3 mm. Anther color: Yellow, RHS 8B. Pollen amount: Scarce. Pollen color: Yellow, RHS 8A.

*Gynoecium* (*on disc and ray florets*).—Pistil number: 1 per floret. Pistil length: About 2 mm. Stigma shape: Cleft. Stigma length: About 1 mm. Stigma color: White, RHS N155D. Style length: About 1 mm. Style color: White, RHS N155D. Ovary diameter: About 2 mm. Ovary color: White, RHS N155D.

Seed: None observed.

Fruit: None observed.

Disease/pest resistance: Resistance to pathogens and pests common to *Asters* has not been observed on plants grown under commercial greenhouse conditions.

Disease/pest susceptibility: Resistance to pathogens and pests common to *Asters* has not been observed on plant grown under commercial green house conditions, except mildew after flowers wilt.

High temperature tolerance: Not specifically tested, but if enough water is available, tolerant up to 35° C.

Low temperature tolerance: Not specifically tested, but if enough water is available, tolerant to −15° C.

I claim:

1. A new and distinct cultivar of *Aster* plant named 'DASDEM', as illustrated and described herein.

* * * * *